US00PP32481P2

(12) United States Plant Patent
Grueber

(10) Patent No.: US PP32,481 P2
(45) Date of Patent: Nov. 17, 2020

(54) ***GERANIUM* PLANT NAMED 'LIBLUMA'**

(50) Latin Name: ***Geranium* hybrid**
Varietal Denomination: LIBLUMA

(71) Applicant: Garry Grueber, Mainz (DE)

(72) Inventor: Garry Grueber, Mainz (DE)

(73) Assignee: Cultivaris GmbH, Heidesheim/Rheinhessen (DE)

( * ) Notice: Subject to any disclaimer, the term of this patent is extended or adjusted under 35 U.S.C. 154(b) by 0 days.

(21) Appl. No.: 16/873,280

(22) Filed: Mar. 9, 2020

(51) Int. Cl.
*A01H 5/02* (2018.01)
*A01H 6/42* (2018.01)

(52) U.S. Cl.
USPC ..... Plt./324
CPC ..... *A01H 6/42* (2018.05)

(58) Field of Classification Search
USPC ..... Plt./324
CPC ..... A01H 6/42
See application file for complete search history.

*Primary Examiner* — Anne Marie Grunberg

(57) ABSTRACT

A new cultivar of *Geranium* plant named 'LIBLUMA' that is characterized by solid blue flowers with purple veins, a long flowering season, good heat tolerance and a mounding plant habit.

1 Drawing Sheet

Botanical classification: *Geranium* hybrid.
Variety denomination: 'LIBLUMA'.

BACKGROUND OF THE INVENTION

The present invention relates to a new and distinct cultivar of *Geranium* plant botanically known as *Geranium* hybrid and hereinafter referred to by the cultivar name 'LIBLUMA'.

Seeds were collected in 2012 from open pollinated *Geranium* plants in a cultivated area of Warmond, The Netherlands. The seeds were subsequently planted in a controlled greenhouse environment and 'LIBLUMA' was discovered and selected by the Inventor in 2013 as a single flowering plant from within the progeny of the stated open pollination in Warmond, The Netherlands. The exact parent plants are unknown.

Asexual propagation of the new cultivar 'LIBLUMA' first occurred by division in 2015 in Heidesheim, Germany. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Geranium* cultivar 'LIBLUMA'. These traits in combination distinguish 'LIBLUMA' as a new and distinct cultivar apart from other existing known varieties of *Geranium*.

1. *Geranium* 'LIBLUMA' exhibits solid blue flowers with purple veins.
2. *Geranium* 'LIBLUMA' exhibits a long flowering season.
3. *Geranium* 'LIBLUMA' exhibits good heat tolerance.
4. *Geranium* 'LIBLUMA' exhibits a mounding plant habit.

The closest comparison cultivars are *Geranium* 'Boo' (U.S. Plant Pat. No. 27,885) and *Geranium* 'Rozanne' (U.S. Plant Pat. No. 12,175). 'LIBLUMA' is distinguishable from 'Boo' by the following characteristics:

1. 'LIBLUMA' exhibits solid blue flowers with purple veins and yellow pollen. In contrast, 'Boo' has mauve-pink flowers with whitish centers, dark violet veins and purple pollen.
2. *Geranium* 'LIBLUMA' exhibits an average of 16 flowers per lateral stem. In contrast, 'Boo' has an average of 5 flowers per lateral stem.
3. *Geranium* 'LIBLUMA' exhibits good heat tolerance. In contrast, 'Boo' is less tolerant of heat.
4. *Geranium* 'LIBLUMA' exhibits a mounding plant habit. In contrast, 'Boo' has a flatter more spreading plant habit.
5. *Geranium* 'LIBLUMA' exhibits peduncles with a length of 8.0 cm. In contrast, 'Boo' has peduncles that are 4.0 cm. in length.

'LIBLUMA' is distinguishable from 'Rozanne' by the following characteristics:

1. 'LIBLUMA' exhibits solid blue flowers with purple veins. In contrast, 'Rozanne' has blue flowers with a vivid blue center eye.
2. *Geranium* 'LIBLUMA' exhibits good heat tolerance. In contrast, 'Rozanne' has poorer heat tolerance.
3. *Geranium* 'LIBLUMA' exhibits a mounding plant habit. In contrast, 'Rozanne' has a more prostrate, trailing plant habit.
5. *Geranium* 'LIBLUMA' exhibits leaf margins that are more serrated than the leaf margins of 'Rozanne'.

BRIEF DESCRIPTION OF THE DRAWING

The accompanying photograph illustrates the distinguishing traits of *Geranium* 'LIBLUMA'. The plant in the photograph shows an overall view of a 2 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Geranium* cultivar named 'LIBLUMA'. Data was collected in Heidesheim, Germany from 2 year old plants in 25 cm. diameter containers. The data was collected in autumn. The plants were grown in a greenhouse from November to April and then outside from May until October. The outdoor temperature range was 15-28 degrees Centigrade during the day and 8-15 degrees Centigrade at night. No growth retardants were used. Color determinations are in accordance with The Royal Horticultural Society Colour Chart 2007 edition, except where general color terms of ordinary dictionary significance are used. The growing requirements are similar to the species. 'LIBLUMA' has not been tested under all possible conditions and phenotypic differences may be observed with variations in environmental, climatic, and cultural conditions, however, without any variance in genotype.

Botanical classification: *Geranium* hybrid 'LIBLUMA'.

Annual or perennial: Perennial.

Parentage: 'LIBLUMA' was discovered amongst an open pollinated population of *Geranium* plants. The exact parent plants are unknown.

Vigor: Strong.

Growth habit: Spreading.

Plant shape: Mounding.

Suitable container size: 25 cm. diameter containers.

Overall plant dimensions: Average 20 cm. in height and 45 cm. in diameter.

Low temperature tolerance: −20° Centigrade.

High temperature tolerance: 40° Centigrade.

Propagation: Division and tissue culture.

Time to initiate roots in summer: 21 days to initiate roots at 20° Centigrade.

Time to initiate roots in winter: 30 days to initiate roots at 20° Centigrade.

Root system: Fine and fibrous.

Stem:

- *Branching habit.*—Basal.
- *Basal branching.*—Yes.
- *Average number of lateral branches.*—20.
- *Pinching.*—Not required.
- *Lateral branch dimensions.*—2.0 mm. in diameter and 45.0 cm. in length.
- *Internode length.*—8.0 cm.
- *Stem texture.*—Smooth.
- *Stem strength.*—Moderate.
- *Stem color.*—144B, sunny side 184C.
- *Pubescence.*—Pilose.

Foliage:

- *Leaf arrangement.*—Opposite.
- *Compound or single.*—Single.
- *Number of leaves per lateral branch.*—Average 10.
- *Leaf shape.*—Palmately divided, lobed and toothed.
- *Leaf apex.*—Acute.
- *Leaf base.*—Oblique.
- *Leaf dimensions.*—4.0 cm. in length and 6.5 cm. in width.
- *Texture.*—Smooth on both sides.
- *Leaf pubescence.*—Short hairs on both surfaces.
- *Leaf margin.*—Dentate.
- *Venation pattern.*—Palmate.
- *Young leaf color* (*upper surface*).—146A.
- *Young leaf color* (*lower surface*).—138B.
- *Mature leaf color* (*upper surface*).—146A.
- *Mature leaf color* (*lower surface*).—138B.
- *Vein color* (*upper surface*).—N144A.
- *Vein color* (*lower surface*).—N144B.
- *Petiole dimensions.*—6.0 cm. in length and 1.5 mm. in diameter.
- *Petiole color.*—144B, sunny side 184C.
- *Durability of foliage to stress.*—Moderate, red dots appear at high temperatures.

Flower:

- *Inflorescence arrangement.*—Axillary racemes with rotate flowers.
- *Inflorescence dimensions.*—12.0 cm. in height and 8.0 cm. in width.
- *Quantity of flowers per inflorescence.*—2.
- *Quantity of flowers per lateral stem.*—4.
- *Quantity of flower buds per lateral stem.*—Average 16.
- *Quantity of flowers and buds per plant.*—Average 50.
- *Natural flowering season.*—July to October.
- *Rate of flower opening.*—Every 2 to 3 days.
- *Fragrance.*—None.
- *Flower bud length.*—10 mm.
- *Flower bud diameter.*—6 mm.
- *Flower bud shape.*—Ovoid.
- *Bud color.*—137C.
- *Rate of bud opening.*—2 to 3 days.
- *Flower aspect.*—Outward.
- *Flower shape.*—Rotate.
- *Flower dimensions.*—4.0 cm. in diameter and 1.2 cm. in height.
- *Number of petals.*—5.
- *Fused or unfused.*—Unfused.
- *Petal arrangement.*—Rotate.
- *Petal shape.*—Obovate.
- *Petal texture.*—Smooth on both surfaces.
- *Petal margin.*—Entire.
- *Petal apex.*—Obtuse.
- *Petal base.*—Obtuse.
- *Petal dimensions.*—1.8 cm. in length and 1.6 cm in width.
- *Petal color when opening* (*upper side*).—93B, veins N80A.
- *Petal color when opening* (*under side*).—93B, veins N80A.
- *Petal color fully opened* (*upper side*).—93B, veins N80A.
- *Petal color fully opened* (*under side*).—93B, veins N80A.
- *Petal color fading to.*—Not fading.
- *Self-cleaning or persistent.*—Self-cleaning.

Calyx:

- *Calyx dimensions.*—1.0 cm. in length and 2.0 cm. in diameter.

Sepals:

- *Sepal arrangement.*—Rotate.
- *Number of sepals.*—5.
- *Sepal shape.*—Ovate.
- *Sepal margin.*—Entire.
- *Sepal apex.*—Acute.
- *Sepal base.*—Attenuate.
- *Sepal dimensions.*—1.2 cm. in length and 0.5 cm. in width.

*Young sepal color* (*upper side*).—143B.
*Young sepal color* (*under side*).—143B.
*Mature sepal color* (*upper side*).—143B.
*Mature sepal color* (*under side*).—143B.

Peduncle:
*Peduncle dimensions*.—8.5 cm. in length and 1.0 mm. in diameter.
*Peduncle angle*.—Upright to 30 degrees from stem.
*Peduncle strength*.—Weak.
*Peduncle color*.—143C.

Pedicels:
*Pedicel dimensions*.—Average 3.5 cm. in length and 1.0 mm. in diameter.
*Pedicel strength*.—Weak.
*Pedicel color*.—143C.

Reproduction organs:
*Stamen number*.—10.
*Anther shape*.—Oblong.
*Anther size*.—2.0 mm. in length.
*Anther color*.—N89A.
*Amount of pollen*.—Low.
*Pollen color*.—1B.
*Pistil number*.—5.
*Pistil length*.—10 mm.
*Stigma shape*.—Linear.
*Stigma color*.—N79A.
*Style length*.—3.5 mm.
*Style color*.—N79C.
*Ovary color*.—143C.

Fruit and seed: Fruit and seed production has not been observed.

Disease and pest resistance: Disease and pest resistance has not been observed.

The invention claimed is:

1. A new and distinct variety of *Geranium* plant named 'LIBLUMA' as described and illustrated.

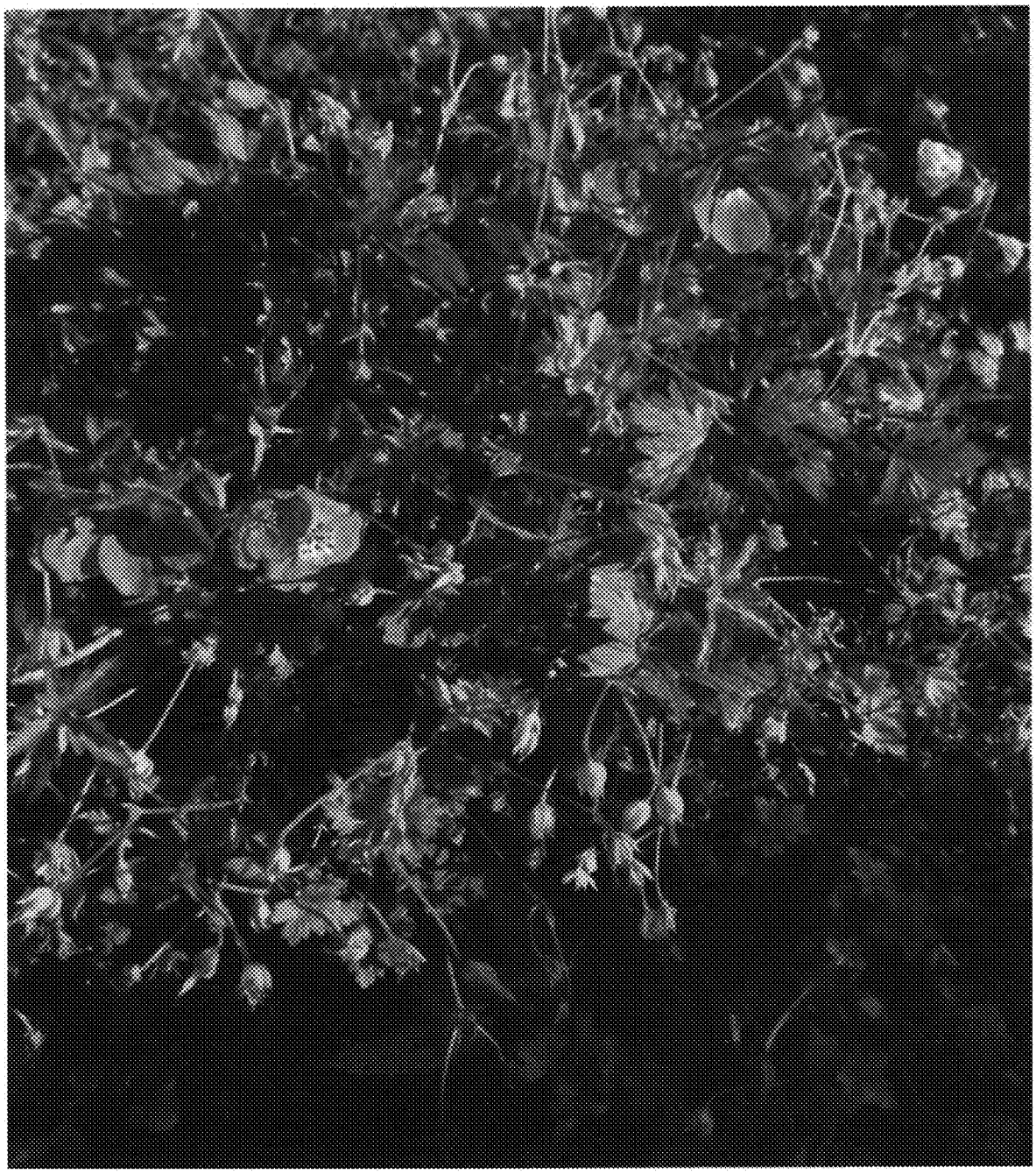

* * * * *